United States Patent [19]

Knaup et al.

[11] Patent Number: 5,171,877
[45] Date of Patent: Dec. 15, 1992

[54] URETHANES MADE FROM ALIPHATIC FLUORO ALCOHOLS, ISOCYANATES AND CARBOXYLIC ACIDS, A PROCESS FOR THEIR PREPARATION AND THEIR USE

[75] Inventors: Wolfgang Knaup, Burgkirchen; Rainer Kupfer, Kastl; Rolf Kleber, Neu-Isenburg; Lothar Jaeckel, Flörsheim; Fritz-Joachim Gohlke, Burgkirchen, all of Fed. Rep. of Germany

[73] Assignee: Hoechst Aktiengesellschaft, Fed. Rep. of Germany

[21] Appl. No.: 633,806

[22] Filed: Dec. 26, 1990

[30] Foreign Application Priority Data

Dec. 28, 1989 [DE] Fed. Rep. of Germany ....... 3943127

[51] Int. Cl.$^5$ ............................................. C07C 261/00
[52] U.S. Cl. ........................................ 560/26; 560/157
[58] Field of Search ................................... 560/26, 157

[56] References Cited

U.S. PATENT DOCUMENTS

| | | | |
|---|---|---|---|
| 4,525,305 | 6/1985 | Patel | 260/401 |
| 4,539,006 | 9/1985 | Langford | 8/94.1 R |
| 4,564,366 | 1/1986 | Patel | 8/94.1 R |
| 4,606,737 | 8/1986 | Stern | 8/115.6 |
| 4,766,234 | 8/1988 | Wehowsky et al. | 560/26 |
| 4,782,175 | 11/1988 | Wehowsky et al. | 560/26 |
| 4,960,543 | 10/1990 | Wehowsky et al. | 560/26 |

*Primary Examiner*—Mukund J. Shah
*Assistant Examiner*—Y. N. Gupta
*Attorney, Agent, or Firm*—Connolly and Hutz

[57] ABSTRACT

The urethanes described are synthesized from aliphatic fluoro alcohols, triisocyanate and a carboxylic acid. They are prepared by reaction of the aliphatic fluoro alcohol with the triisocyanate to give the fluoro alcohol/triisocyanate adduct and by reaction of this adduct with the carboxylic acid. The new urethanes are preferably used for the finishing of textiles for the purpose of achieving water, oil and soil repellency.

2 Claims, No Drawings

URETHANES MADE FROM ALIPHATIC FLUORO ALCOHOLS, ISOCYANATES AND CARBOXYLIC ACIDS, A PROCESS FOR THEIR PREPARATION AND THEIR USE

The invention relates to urethanes made from aliphatic fluoro alcohols, isocyanates and carboxylic acids. The invention furthermore relates to a process for the preparation of these urethanes and to their use.

It has been known for a long time to improve the properties of urethanes made from aliphatic fluoro alcohols and mono- or polyisocyanates with respect to the finishing of textiles, leather, wood and the like by incorporating a modifying group. Over the course of time, many compounds have been described as modifying components, also including carboxylic acids.

Thus, U.S. Pat. No. 4,525,305 describes urethanes formed from an aliphatic fluoro alcohol which can also contain an epichlorohydrin group, a diisocyanate and an aliphatic amino- or hydroxy-monocarboxylic acid as modifying component (cf., in particular, column 6, scheme 1 and scheme 2, and the urethane compounds in Table 1). Similar urethane compounds are also described in U.S. Pat. No. 4,539,006 (cf. in particular, column 4, lines 42/43, and scheme 4, columns 7 and 8). The urethanes disclosed in both U.S. Pat. No. 4,525,305 and 4,539,006, which are said to be suitable in particular for the finishing of leather, obviously have, apart from the aliphatic monocarboxylic acid mentioned, also the following two characteristic features: they all contain a sulfonamido group and exclusively diisocyanates as the isocyanate.

The more recent U.S. Pat. No. 4,782,175 describes urethanes made from an aliphatic fluoro alcohol which contains up to 10 epichlorohydrin units, a diisocyanate or a triisocyanate and an aromatic amino- or hydroxymonocarboxylic acid (cf., in particular, column 3, lines 31 to 34, and formula B12 in the Table). These urethanes are recommended as finishing agents for textiles and leather.

The prior art thus shows that aliphatic and aromatic monocarboxylic acids have been used as modifying components for the preparation of urethane compounds already several times and that urethanes of this type are supposedly more or less good finishing agents for textiles and leather.

The object of the invention is to produce urethanes from aliphatic fluoro alcohols, isocyanates and carboxylic acids which, compared with the prior art, represent improved finishing agents, in particular for textiles.

The urethanes according to the invention are based on the surprising finding that selected aliphatic, aromatic and cycloaliphatic mono- and polycarboxylic acids are particularly effective modifying components if they are combined with an aliphatic fluoro alcohol and with a triisocyanate and that an even higher efficiency is achieved if, apart from one or more free —COOM groups (M=H or a base radical) and the triisocyanate, also epichlorohydrin groups are present in the urethane molecule. In particular textile materials are given very high oleophobic and hydrophobic values by the urethanes according to the invention. This is an unexpected result, especially since the U.S. Pat. Nos. 4,525,305 and 4,539,006 mentioned point out repeatedly that the urethanes described, which are made from a fluoro alcohol, aliphatic carboxylic acid and diisocyanate, are said to be efficient especially for leather. Surprisingly, the urethane compounds according to the invention have a further very useful property, namely that of repelling solid dirt, such as dust (street dust), soot and the like.

The urethane compounds according to the invention have the formula 1 below

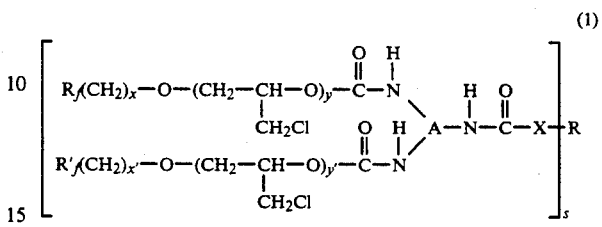

in which the symbols have the following meanings:

$R_f$ and $R'_f$ are each a perfluoroalkyl group having 4 to 22 carbon atoms, preferably 6 to 18 carbon atoms; $R_f$ and $R'_f$ preferably have the same meaning, x and x' are each a number from 1 to 4, preferably 2; x and x' preferably have the same meaning, y and y' are each a number from 0 to 7, preferably 0 to 4; preferred meanings of y and y' are that both indices are each a number from 1 to 7, preferably 1 to 4, or that one of the two indices is 0 and the other a number from 1 to 7, preferably 1 to 4, A is a radical of an aliphatic, aromatic or cycloaliphatic triisocyanate, R is a radical of an aromatic, aliphatic or cycloaliphatic carboxylic acid or the salt of a carboxylic acid having 1 to 5 —COOM groups in which M is hydrogen or a base radical, X is —O—, a single bond (direct bond) or —NR'—, in which R' is H, $C_1$ to $C_4$-alkyl or —$CH_2COOM$ in which M has the meaning mentioned, and s is a number from 1 to 3, with the proviso that the urethane compounds where $R_f$ and $R'_f$ are each ($C_8F_{17}$—$C_{16}F_{33}$)—, x and x' and y and y' are each 2, A is a triisocyanate radical of the formula below,

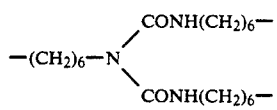

X is —O— or —NH—, R is an aromatic carboxylic acid radical of the formula below

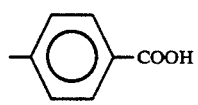

and s is 1 are excepted.

The excepted urethane compounds are evident from the U.S. Pat. No. 4,782,175 mentioned (cf. Patent claim 1 and formula B12 in the table).

The perfluoroalkyl group $R_f$ and $R'_f$ can be linear or branched, saturated or unsaturated (preferably having 1 to 3 double bonds), saturated being preferred. In the case of a branched perfluoroalkyl group, the terminal-branched group is preferred. The perfluoroalkyl radical is frequently a mixture of perfluoroalkyl having the number of carbon atoms mentioned.

A is the radical of a triisocyanate. This is an essential feature of the urethanes according to the invention. The type and structure of the triisocyanate (which forms the radical A) can be varied within wide limits. Thus, aliphatic, aromatic and cycloaliphatic, preferably aliphatic and aromatic, triisocyanates are suitable. The triisocyanates in question are known and commercially available. Below, examples of representatives of A in the form of triisocyanates are given by way of the formula, i.e. formulae 2 to 7:

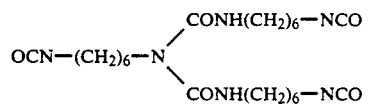
(2)

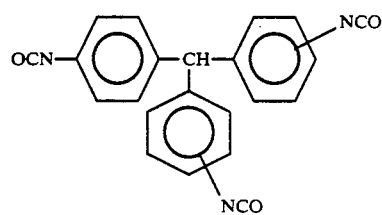
(3)

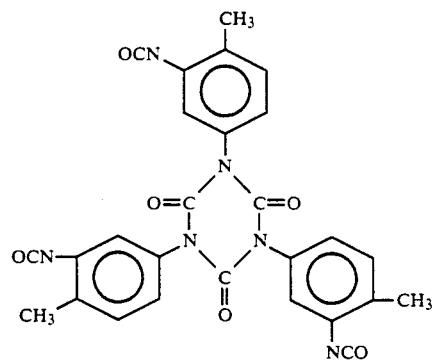
(4)

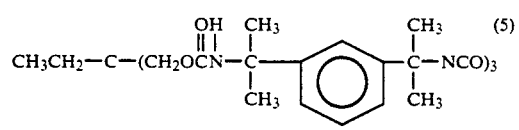
(5)

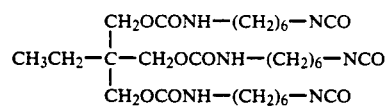
(6)

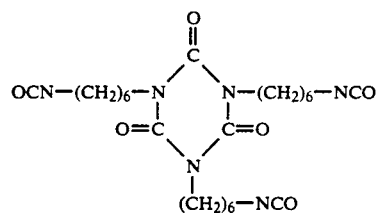
(7)

The triisocyanate radicals which follow from formulae 2, 6 and 7 are particularly preferred representatives of A.

R is preferably (a) a radical of an aromatic carboxylic acid or of the salt of an aromatic carboxylic acid of formulae 8 and 9 below:

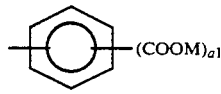
(8)

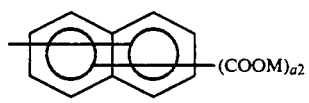
(9)

in which M has the meaning mentioned and a1 and a2 are each a number from 1 to 5, preferably 1, 2 or 3, or (b) a radical of an aliphatic carboxylic acid or the salt of an aliphatic carboxylic acid of formula 10 below

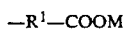
(10)

in which M has the meaning given and $R^1$ is a (saturated or unsaturated, substituted or unsubstituted) aliphatic hydrocarbon radical having at most 15 carbon atoms; $R^1$ is preferably a (linear or branched, saturated or unsaturated) alkylene radical having at most 10 carbon atoms, —$(CH_2)_z$—radicals where z is an integer from 1 to 10 being preferred, or a radical of formulae 11 to 13 below:

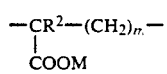
(11)

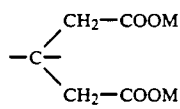
(12)

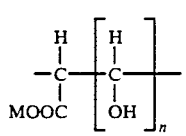
(13)

in which M has the meaning mentioned, m is 0 or an integer from 1 to 7, n is 1, 2 or 3, and $R^2$ is H, OH or $C_1$ to $C_4$-alkyl.

Below, examples of representatives of R are given in the form of the acid, i.e. formulae 14 to 26:

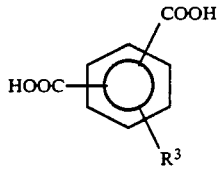
(14)

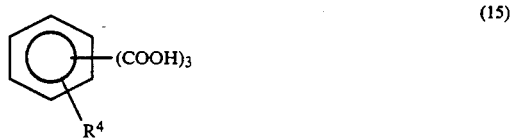
(15)

(16)

-continued $$\underset{\text{(17)}}{\bigcirc}-(COOH)_6$$

$$\underset{\text{(18)}}{\bigcirc\bigcirc}\begin{matrix}-COOH\\-COOH\\R^6\end{matrix}$$

in which $R^3$, $R^4$, $R^5$, $R^6$ are H, OH or $NH_2$, $HO-(CH_2)_z-COOH$ (19)
i.e. hydroxyalkylenecarboxylic acids, $H_2N-(CH_2)_z-COOH$ (20)
i.e. aminoalkylenecarboxylic acids, $HOOC-(CH_2)_z-COOH$ (21)
i.e. alkylenedicarboxylic acids, in which z has in each case the meaning mentioned, and is preferably 1 to 5, $HOOC-CH=CH-COOH$ (22)

$$\underset{\text{COOH}}{HO-CR^2-(CH_2)_m-COOH}$$ (23)

in which $R^2$ and m have the meanings mentioned, 0, 1, 2 or 3 being preferred for m and H being preferred for $R^2$, i.e. hydroxyalkylenedicarboxylic acids, such as tartronic acid ($R^2$=H, m=0), malic acid ($R^2$=H, m=1) and the like, $$\underset{\text{COOH}}{H_2N-CR^2-(CH_2)_m-COOH}$$ (24)

in which $R^2$ and m have the meaning mentioned under formula 23, i.e. aminoalkylenedicarboxylic acids, $$HO-C\begin{matrix}-CH_2-COOH\\-COOH\\-CH_2-COOH\end{matrix}$$ (25)

citric acid $$HO-\underset{HOOC}{\overset{H}{\underset{|}{C}}}-\left[\underset{OH}{\overset{H}{\underset{|}{C}}}\right]_n-COOH \quad n=1,2,3$$ (26)

sugar acids, for example tartaric acid (n = 1)

Particularly preferred radicals R of a carboxylic acid or the salt of a carboxylic acid are those resulting from the acids of the formulae 14 to 16, 19 to 21, 23 and 25.

X is preferably —O— (i.e. an HO group supplies the active H atom for the reaction with the NCO group) or is —NR'— in which R' is H or $C_1$ to $C_4$-alkyl (i.e. an amino group or a substituted amino group supplies the active H atom), or is a single bond which is also called a direct bond (i.e. a COOH group supplies the active H atom, in which the result of the reaction with the NCO group is the formation of $CO_2$, leading to a single bond).

s is preferably 1, 2 or 3, with the proviso that in the case where X is —O— or —NR'— s is 1, R' being H or $C_1$ to $C_4$-alkyl.

M is preferably H or a base radical selected from the group comprising an alkali metal ion, ammonium ion and organoammonium ion, such as K, Na, $NH_4$, $H_2N(C_2H_5)_2$, $HN(CH_3)_3$, $H_3N(C_2H_4OH)$, $H_2N(C_2H_4OH)_2$, $HN(C_2H_4OH)_3$, $H_3N(C_{12}H_{25})$ and the like.

As for the meanings of y and y' in formula 1, it is preferred, as already mentioned, that (a) both y and y' are a number from 1 to 7, preferably a number from 1 to 4, or that (b) either y or y' is 0 and the other is a number from 1 to 7, preferably 1 to 4; variation (b) is particularly preferred. The reason is that it has been found that the urethanes of the formula 1 according to the invention are particularly efficient if one of the two fluoro alcohol strands bound to the triisocyanate is free of epichlorohydrin but the other contains epichlorohydrin, specifically 1 to 7, preferably 1 to 4, epichlorohydrin units.

The preparation of the urethanes according to the invention follows from formula 1 and is described in more detail below. They are prepared by reacting 1 to 3 mol of a fluoro alcohol/triisocyanate adduct of the formula 27

$$\begin{matrix}R_f(CH_2)_x-O-(CH_2-\underset{CH_2Cl}{\overset{|}{CH}}-O)_y-\overset{O}{\overset{\|}{C}}-\overset{H}{\underset{|}{N}}\\ \phantom{xxxxxxxxxxxxxxxxxxxxxxxxxxxx}\overset{O}{\overset{\|}{C}}-\overset{H}{\underset{|}{N}}\diagup A-NCO\\ R'_f(CH_2)_{x'}-O-(CH_2-\underset{CH_2Cl}{\overset{|}{CH}}-O)_{y'}-\overset{O}{\overset{\|}{C}}-\overset{H}{\underset{|}{N}}\end{matrix}$$ (27)

in which $R_f$, $R'_f$, x, x', y, y' and A have the meanings mentioned with 1 to 3 mol of an aromatic, aliphatic or cycloaliphatic carboxylic acid, in which the desired urethane is obtained in the form of an acid by the addition of 1 to 3 H atoms of the carboxylic acid compound in the form of —OH, —NHR', where R' has the meaning mentioned, or of —COOH to the —NCO group of the adduct, from which the desired urethane is obtained in the form of a salt by neutralization with a base.

The fluoro alcohol/triisocyanate adducts to be used are known. They are described in U.S. Pat. No. 4,782,175 mentioned at the beginning. They are prepared by reacting the aliphatic fluoro alcohol present in the adduct with a triisocyanate corresponding to the radical A in formula 27. The reaction is preferably carried out at atmospheric pressure without solvent or with the use of an inert solvent. Suitable solvents are halogenated hydrocarbons, such as carbon tetrachloride (boiling point 77° C.), dichloroethane (boiling point 84° C.) and trifluorotrichloroethane (boiling point 48° C.), ketones, such as acetone (56° C.), methyl ethyl ketone (80° C.) and diethyl ketone (101° C.), ethers, such as diisopropyl ether (68° C.), tetrahydrofuran (66° C.) and dibutyl ether (142° C.) and esters, such as ethyl acetate (77° C.) and butyl acetate (123° C.). In particular when a solvent is used, it is preferred to use Lewis acids as the catalyst. The type of Lewis acid is not critical. Suitable Lewis acids are $BF_3$, boron trifluoride diethyl etherate, $SnCl_4$, $SbCl_5$, $TiCl_4$, $FeCl_3$, $PF_3$ and dibutyltin dilaurate, boron trifluoride diethyl etherate and dibutyltin dilaurate being preferred. The amount of Lewis acid is in general 0.01 to 3% by weight, preferably 0.1 to 1% by weight, relative to the amount of fluoro alcohol used. The reaction temperature can be varied within wide limits, and as a rule it is in the range from 50° to 150° C. It is preferred to carry out the reaction at the boiling point temperature of the solvent used. The reaction time is from. 1 to 5 hours. The reaction proceeds quantitatively. The fluoro alcohol/triisocyanate adduct obtained is in general a wax-like and colorless or slightly yellow to brown product.

The reaction of the fluoro alcohol/triisocyanate adduct with the aliphatic, aromatic or cycloaliphatic carboxylic acid is preferably carried out in such a manner that the adduct and the carboxylic acid are initially introduced into a reaction vessel, and the mixture is kept at a temperature of 50° to 150° C., preferably 70° to 120° C., with stirring until no more free NCO groups are present (the course of the reaction can be monitored, for example, by infrared spectroscopy). The reaction is preferably carried out at atmospheric pressure without a solvent or with the use of an inert solvent. The abovementioned solvents are also suitable here. The presence of a Lewis acid is advantageous for the course of the reaction. The abovementioned Lewis acids are also suitable here. The amount of Lewis acid is in general 0.01 to 3% by weight, preferably 0.1 to 1% by weight, relative to the adduct used. The reaction time is in the range of 1 to 8 hours. The reaction proceeds quantitatively. The reaction products obtained are the urethanes according to the invention in the form of the acid, i.e. M is H. They are in general solid to wax-like, colorless or yellow to brown products. The solvent used for the reaction can be removed without difficulties by distillation, if the urethanes are desired in solid form.

The conversion of the urethanes in the form of the acid into those in the form of salts is achieved by neutralizing the first-mentioned compounds with a base, preferably with an alkali metal hydroxide, such as sodium hydroxide or potassium hydroxide, with an alkali metal alcoholate, such as alkali metal methoxide, ethoxide or isopropoxide, or with ammonium hydroxide or an organoammonium compound of the abovementioned type. The bases are preferably used in the form of a 10% to 50% strength by weight aqueous solution. The urethanes according to the invention in the salt form are present as a rule as 20% to 70% strength by weight aqueous solutions or as a solid, i.e. substantially free of water or other solvents.

The active H atom in the reaction of the carboxylic acid with the fluoro alcohol/triisocyanate adduct originates, as already mentioned, from a HO group, HNR' group or COOH group which is present in the mono- or polycarboxylic acids used. It has been found that the readiness to release an active H atom in general increases in the following order: carboxyl group, hydroxyl group, amino or substituted amino group. This means that in the case of COOH groups and HO groups in the carboxylic acid used, which is for example true of citric acid, the HO group is the preferred supplier of the H atom. The same is true in the case of COOH and amino or substituted amino groups.

The new urethanes ar used according to the invention for the finishing of textiles. They give textiles excellent hydrophobicity and oleophobicity. Furthermore, they have the property of withstanding without significant loss of efficiency the severe stresses to which the finished textiles are exposed, for example during drawing, texturing and in particular dyeing and washing. A further advantage of the urethanes according to the invention is that they can also be used in conventional textile treatment compositions, for example in spin finish, and do not lose their excellent effect as a result of this. The particular distinction of the new urethanes is the finding that, in addition to the properties mentioned, they also have so-called effect of dry-soil repellency, i.e. the textiles treated with the urethanes according to the invention also repel solid dirt, such as street dust, soot and the like; this dirt is also not attracted, let alone absorbed, by the treated textiles. This means that the urethanes according to the invention give the textile materials an unexpectedly advantageous combination of properties.

The textile material can be of natural and/or synthetic nature. It is preferably made of cotton, polyamide, polyester and/or polyacrylonitrile, polyamide being particularly preferred. The textile material can be present in any desired form, for example as filament, fiber, yarn, fabric, carpet or fleece. The amount applied of the compound according to the invention is selected such that 0.05% to 1.5% by weight of fluorine, preferably 0.1% to 1% by weight of fluorine, are present on the textile material, the percentages by weight being based on the treated textile material. The urethanes according to the invention are applied to the textile material, as a rule, either during one of the conventional textile treatments by means of finishing compositions, in which the urethane according to the invention has been incorporated in the finishing composition, or by means of solutions, emulsions or dispersions formed during the preparation of the urethane or especially prepared. In the textile treatment compositions, for example spin finishes, the urethanes according to the invention are present in a concentration of 0.5% to 5% by weight, preferably 1% to 3% by weight. In the solutions, emulsions or dispersions, they are present in a concentration of 5% to 40% by weight, preferably 8% to 30% by weight. The treatment of the textiles with the solutions, emulsions or dispersions is carried out by conventional methods, for example by spraying, dipping, padding and the like. The impregnated textile material is then dried and subjected to a heat treatment. The heat treatment (also called condensation) is, as a rule, carried out in such a manner that the textile material is heated to a temperature of 130° to 200° C. and maintained at this temperature for 10 seconds to 10 minutes. The textile material finished with the urethanes according to the invention has the abovementioned excellent properties The invention is now illustrated in more detail by way of examples.

COMPOUNDS ACCORDING TO THE INVENTION

In the examples for preparing the urethanes according to the invention, the following fluoro alcohols/triisocyanate adducts were used:

Adduct 1:

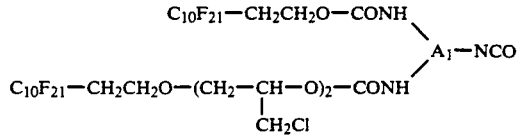

-continued

Adduct 2:

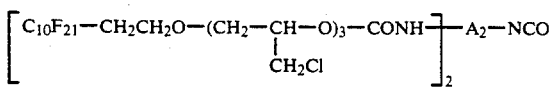

Adduct 3:

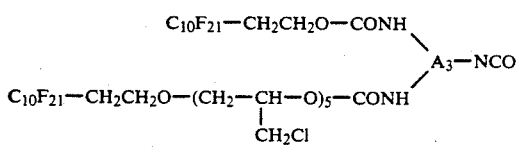

Adduct 4:

$C_{10}F_{21}$—$CH_2CH_2O$—$CONH$
$\diagdown$
$A_3$—NCO
$\diagup$
$C_{10}F_{21}$—$CH_2CH_2O$—$(CH_2$—$CH$—$O)_5$—$CONH$
                                    |
                                   $CH_2Cl$ $A_1$ is a triisocyanate radical corresponding to the triisocyante of formula 2.

$A_2$ is a triisocyanate radical corresponding to the triisocyanate of formula 6.

$A_3$ is a triisocyanate radical corresponding to the triisocyanate of formula 7.

The perfluoroalkyl radical $C_{10}F_{21}$— in the fluoro alcohol of adducts 1 to 4 is a $(C_8F_{17}$—$C_{16}F_{33})$ mixture named in short $C_{10}F_{21}$—.

Since fluoro alcohol/triisocyanate adducts and their preparation are part of the prior art and a preferred preparation procedure has already been described above, further discussion of the adducts 1 to 4 mentioned and used in the examples below seems to be superfluous.

EXAMPLE 1

85.0 g (0.021 mol) of adduct 1 and 4.1 g (0.021 mol) of citric acid in powder form and 30 g of methyl ethyl ketone as solvent (dispersant) and 3 drops of dibutyltin dilaurate as catalyst were initially introduced into a reaction vessel which was equipped with a stirrer, thermometer and a reflux condenser with drying tube. The mixture was heated to 80° C. (boiling temperature of methyl ethyl ketone) and kept at this temperature for 4 hours with stirring, during which adduct 1 and citric acid reacted to give the desired urethane compound according to the invention. The urethane obtained in a yield of 95.8% of theory (a wax-like, yellow-colored product) is shown in Table 1 below by way of its formula; formula B1.

EXAMPLE 2

The procedure of Example 1 is repeated, using 278.1 g (0.070 mol) of adduct 1 and 5.3 g (0.070 mol) of glycolic acid ($HOCH_2COOH$). The yield of urethane compound was 94.4% of theory; formula B2.

EXAMPLE 3

The procedure of Example 1 was repeated, using 85.0 g (0.021 mol) of adduct 1 and 3.8 g (0.021 mol) of the following aromatic aminodicarboxylic acid

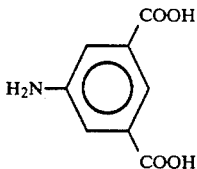

The urethane compound formed from adduct 1 and the aminodicarboxylic acid was converted to the corresponding sodium salt. For this purpose, the reaction product obtained after the four-hour reaction of adduct 1 and aminodicarboxylic acid was treated with sodium methoxide (i.e. 7.6 g) in the form of a 30% strength by weight methanolic solution, and the mixture was kept at a temperature in the range from 40° to 60° C. for 30 minutes with stirring. The yield of urethane compound in the form of a sodium salt (a wax-like yellow-colored product) was 97.1% of theory; formula B3.

EXAMPLE 4

The procedure of Example 3 was repeated, using 85.0 g (0.021 mol) of adduct 1 and 4.3 g (0.021 mol) of aminoundecanoic acid and maintaining the mixture at the 80° C mentioned for 8 hours with stirring. The yield of urethane compound in the form of a sodium salt was 96.6% of theory; formula B4.

EXAMPLE 5

The procedure of Example 4 was repeated, using 150.0 g (0.048 mol) of adduct 1 and 6.3 g (0.048 mol) of aminocaproic acid. The yield of urethane compound in the form of a sodium salt was 98.4% of theory; formula B5.

EXAMPLE 6

The procedure of Example 1 was repeated, using 270.6 g (0.069 mol) of adduct 2 and 7.3 g (0.023 mol) of the following benzenetetracarboxylic acid

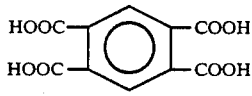

The yield of urethane compound was 97.9% of theory; formula B6.

EXAMPLE 7

The procedure of Example 1 was repeated, using 245.0 g (0.063 mol) of adduct 1 and 9.2 g (0.063 mol) of adipic acid and maintaining the mixture at the 80° C. mentioned for 10 hours with stirring. The yield of urethane compound was 96.9% of theory; formula B7.

EXAMPLE 8

The procedure of Example 2 was repeated. The urethane compound formed from adduct 1 and glycolic acid was converted to the corresponding salt with monoethanolamine. For this purpose, the reaction product obtained after the reaction of adduct 1 and glycolic acid was treated with the required amount of monoethanolamine ($H_2NCH_2CH_2OH$), and the mixture was kept at a temperature in the range from 40° to 60° C. for 30 minutes with stirring. The yield of urethane compound in the form of an ethanolamine salt (a more or less powdered, yellow-colored product) was 98.0% of theory; formula B8.

EXAMPLE 9

The procedure of Example 8 was repeated, carrying out the salt formation with dodecylmonoamine ($H_2NC_{12}H_{25}$). The yield of urethane compound in the form of a dodecylamine salt (a more or less powdered, yellow-colored product) was 8.0% of theory; formula B9.

EXAMPLE 10

The procedure of Example 6 was repeated, using 50.5 g (0.0094 mol) of adduct 2 and 1.5 g (0.0047 mol) of benzenetetracarboxylic acid. The yield of urethane compound was 97.5% of theory; formula B10.

EXAMPLE 11

The procedure of Example 1 was repeated, using 102.0 g (0.024 mol) of adduct 3 and 4.6 g (0.024 mol) of malic acid. The yield of urethane compound was 97.5% of theory; formula B11.

EXAMPLE 12

The procedure of Example 1 was repeated, using 90.0 g (0.019 mol) of adduct 4 and 3.7 g (0.019 mol) of citric acid. The yield of urethane compound was 97.8% of theory; formula B12.

TABLE 1

| No. | Formulae of the urethanes according to the invention of Examples 1 to 12 |
|---|---|
| B1 | $C_{10}F_{21}-CH_2CH_2O-CONH$ \ $A_1-NHCO-O-C(CH_2COOH)_2-COOH$ / $C_{10}F_{21}-CH_2CH_2O-(CH_2-CH(CH_2Cl)-O)_2-CONH$ |
| B2 | $C_{10}F_{21}-CH_2CH_2O-CONH$ \ $A_1-NHCO-O-CH_2COOH$ / $C_{10}F_{21}-CH_2CH_2O-(CH_2-CH(CH_2Cl)-O)_2-CONH$ |
| B3 | $C_{10}F_{21}-CH_2CH_2O-CONH$ \ $A_1-NHCO-NH-C_6H_3(COONa)_2$ / $C_{10}F_{21}-CH_2CH_2O-(CH_2-CH(CH_2Cl)-O)_2-CONH$ |
| B4 | $C_{10}F_{21}-CH_2CH_2O-CONH$ \ $A_1-NHCO-NH-(CH_2)_{10}-COONa$ / $C_{10}F_{21}-CH_2CH_2O-(CH_2-CH(CH_2Cl)-O)_2-CONH$ |
| B5 | $C_{10}F_{21}-CH_2CH_2O-CONH$ \ $A_1-NHCO-NH-(CH_2)_5-COONa$ / $C_{10}F_{21}-CH_2CH_2O-(CH_2-CH(CH_2Cl)-O)_2-CONH$ |
| B6 | $[(C_{10}F_{21}-CH_2CH_2O-CONH)_2-A_1-NHCO]_3-C_6H_3-COOH$ |
| B7 | $C_{10}F_{21}-CH_2CH_2O-CONH$ \ $A_1-NHCO-(CH_2)_4-COOH$ / $C_{10}F_{21}-CH_2CH_2O-(CH_2-CH(CH_2Cl)-O)_2-CONH$ |
| B8 | $C_{10}F_{21}-CH_2CH_2O-CONH$ \ $A_1-NHCO-O-CH_2COONH_3(C_2H_4OH)$ / $C_{10}F_{21}-CH_2CH_2O-(CH_2-CH(CH_2Cl)-O)_2-CONH$ |

TABLE 1-continued

| No. | Formulae of the urethanes according to the invention of Examples 1 to 12 |
|---|---|
| B9 | $C_{10}F_{21}-CH_2CH_2O-CONH$<br>$\phantom{xxxxxxxxxxxxxxxxxxxxxxxxxxx}\diagdown$<br>$\phantom{xxxxxxxxxxxxxxxxxxxxxxxxxxxxxx}A_1-NHCO-O-CH_2COONH_3(C_{12}H_{25})$<br>$\phantom{xxxxxxxxxxxxxxxxxxxxxxxxxxx}\diagup$<br>$C_{10}F_{21}-CH_2CH_2O-(CH_2-CH-O)_2-CONH$<br>$\phantom{xxxxxxxxxxxxxxxxxxxx}\vert$<br>$\phantom{xxxxxxxxxxxxxxxxxxxx}CH_2Cl$ |
| B10 | $[(C_{10}F_{21}-CH_2CH_2O-CONH)_2-A_1-NHCO]_2-\bigcirc-(COOH)_2$ |
| B11 | $\left[C_{10}F_{21}-CH_2CH_2O-(CH_2-CH-O)_3-CONH\right]_2-A_2-NHCO-O-CHCH_2COOH$<br>$\phantom{xxxxxxxxxxxxxxxxxxxxxxxxxxx}\vert\phantom{xxxxxxxxxxxxxxxxxxxxxxxxxxxxxxxxxxxxxxxxxxxxx}\vert$<br>$\phantom{xxxxxxxxxxxxxxxxxxxxxxxxxxx}CH_2Cl\phantom{xxxxxxxxxxxxxxxxxxxxxxxxxxxxxxxxxx}COOH$ |
| B12 | $C_{10}F_{21}-CH_2CH_2O-CONH\phantom{xxxxxxxxxxxxxxxxxxx}CH_2COOH$<br>$\phantom{xxxxxxxxxxxxxxxxxxxxxxxxxxx}\diagdown\phantom{xxxxxxxxxxxxxxxxxxxxxx}\vert$<br>$\phantom{xxxxxxxxxxxxxxxxxxxxxxxxxxxxxx}A_3-NHCO-O-C-COOH$<br>$\phantom{xxxxxxxxxxxxxxxxxxxxxxxxxxx}\diagup\phantom{xxxxxxxxxxxxxxxxxxxxxx}\vert$<br>$C_{10}F_{21}-CH_2CH_2O-(CH_2-CH-O)_5-CONH\phantom{xxxxxxxxxxx}CH_2COOH$<br>$\phantom{xxxxxxxxxxxxxxxxxxxx}\vert$<br>$\phantom{xxxxxxxxxxxxxxxxxxxx}CH_2Cl$ |

USE OF THE COMPOUNDS ACCORDING TO THE INVENTION

Examples I to XII

In Examples I to XII, the compounds according to the invention B1 to B12 were tested by means of a conventional spin finish for polyamide fibers each containing about 150 g of the compound according to the invention per 1,000 g of spin finish (thus, the spin finish comprised water as the main component, the conventional ethoxylated fatty alcohols and the long-chain amine oxides as finishing compositions and about 15% by weight of the compound according to the invention). In each case, identical nylon-6 filaments were treated with each of the twelve spin finishes in order to apply such an amount of the compound according to the invention and the finishing composition to the filaments that 0.05% by weight of fluorine and 1% by weight of finishing composition were present on the filaments, the percentages by weight in each case being based on the weight of the filament. For this purpose, the filaments were led in a conventional manner through the spin finish, dried and kept at a temperature of 200° C. for 30 seconds (heat treatment, condensation). The filaments thus treated were used to produce in each case a fabric. Twelve fabrics containing the compounds according to the invention B1 to B12 were present, in which on each fabric a fluorine deposit of 0.05% by weight and a finishing composition deposit of 1% by weight were present, the percentages by weight in each case being based on the weight of the fabric.

The oil-repellency (oleophobicity) according to AATCC test standard 118-1966, the water repellency (hydrophobicity) according to DIN 53888 -1965 and the soiling (dry-soil repellency) according to the method described below of the twelve fabrics were tested after the condensation mentioned and after a three-hour treatment of the condensed fabric with an alkaline wash at the boil. In this treatment, the individual fabrics were boiled in the usual manner in an alkaline wash liquid for 3 hours and then dried; the wash liquid comprised 1 l of water, 1 g of trisodium phosphate and 2 g of a fatty acid polyglycol ester obtained by ethoxylation of 1,4-butanediol with 15 mol of ethylene oxide, followed by esterification of the ethoxylate with 1 mol of oleic acid.

The results from Examples I to XII are summarized in Table 2 below.

TABLE 2

| Examples and compounds tested | Oil repellency | | Water repellency | | Soiling | |
|---|---|---|---|---|---|---|
| | after condensation | after wash at the boil | after condensation | after wash at the boil | after condensation | after wash at the boil |
| I/B1 | 6 | 5 | 5 | 5 | 3 | 4 |
| II/B2 | 6 | 5 | 5 | 5 | 3 | 4 |
| III/B3 | 6 | 5 | 5 | 5 | 3 | 4 |
| IV/B4 | 6 | 6 | 5 | 5 | 3 | 3 |
| V/B5 | 6 | 5 | 5 | 5 | 3 | 4 |
| VI/B6 | 5 | 4 | 5 | 4 | 3 | 3 |
| VII/B7 | 6 | 5 | 6 | 5 | 3 | 3 |
| VIII/B8 | 6 | 5 | 5 | 4 | 3 | 4 |
| IX/B9 | 6 | 5 | 5 | 4 | 3 | 4 |
| X/B10 | 5 | 4 | 5 | 4 | 3 | 3 |
| XI/B11 | 5 | 4 | 5 | 4 | 3 | 4 |
| XII/B12 | 6 | 5 | 6 | 5 | 3 | 4 |

In what follows, the AATCC test 118 - 1966 (American Association of Textile Chemists and Colorists), DIN 53 888 - 1965 (German Technical Standard) and the determination of wet soiling are described.

As is known, the oil repellency value according to AATCC test 118 - 1966 is determined by placing 3 drops of a specific test liquid (see below) carefully on the textile material to be tested. Time of exposure: 30 seconds. The value observed is that at which not yet apparent wetting of the fabric underneath the drop (after the time of exposure has expired) has been caused:

| Test liquid | Oil repellency value |
|---|---|
| Paraffin oil | 1 |
| Paraffin oil:n-hexadecane = 65:35 | 2 |
| n-Hexadecane | 3 |
| n-Tetradecane | 4 |
| n-Dodecane | 5 |
| n-Decane | 6 |
| n-Octane | 7 |
| n-Heptane | 8 |

An oil repellency value of 1 denotes the poorest and an oil repellency value of 8 the best effect.

As is known, the water repellency value according to DIN 53 888 - 1965 is determined by a rain shower test of the textiles to be tested under standardized conditions, the bottom side of the textile specimen being rubbed mechanically at the same time. The water-repellency effect is evaluated visually by a rating of 1 to 5, a rating of 1 denoting the poorest and a rating of 5 the best water repellency effect.

The soiling was determined by the following method: the textile material to be tested was treated in a rotating drum at 60° C. with a soiled liquor for 45 minutes. The soiled liquor comprises 2 g of a conventional heavy-duty detergent and 1 g of dirt in 1 l of water. The dirt is a mixture of street dust having a particle size of at most 0.4 μm as main component and 3% by weight (relative to street dust) of powdered soot. The drum which is rotating during the 45 minutes mentioned contains 50 parts by weight of soiled liquor per 1 part by weight of textile material to be tested. The textile material thus treated is rinsed with water and dried in a drying cabinet at 50° C. The soiled and dried textile material is then subjected to washing. For this purpose, it is treated in a rotating drum at 60° C. with a clean liquor for 30 minutes. The clean liquor comprises 2 g of the heavy-duty detergent used in the first treatment in 1 l of water. The drum which is rotating during the 30 minutes mentioned contains 50 parts by weight of clean liquor per 1 part by weight of the textile material used for washing. The textile material thus washed is rinsed with water and dried in a drying cabinet at 50° C. The gray scale of the textile material now present is evaluated visually and by a rating of 1 to 5; a rating of 1 is the poorest result (i.e. the textile material has a gray appearance due to still adhering dirt), while a rating of 5 is the best result (i.e. the textile material is completely free of dirt).

The test results show that, apart from a high oil and water repellency, also a surprisingly high soil repellency is achieved by means of the urethanes according to the invention.

What is claimed is:

1. A urethane of the formula

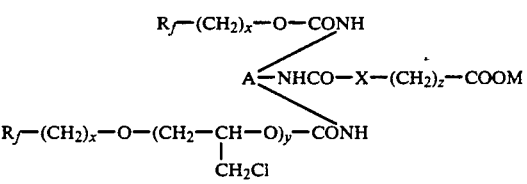

wherein
$R_f$ is a perfluoroalkyl group having 6 to 18 carbon atoms,
x is 1 to 4,
y is 1 to 7,
A is a triisocyanate radical of the formula

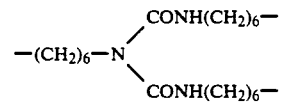

X is —O— or —NH—,
z is 1 to 10, and
M is a member selected from the group consisting of H, alkali metal ions, ammonium ion, and organoammonium ions.

2. A urethane of the formula

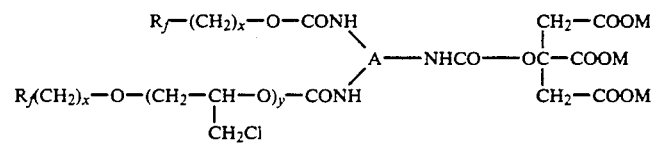

wherein
$R_f$ is a perfluoroalkyl group having 6 to 18 carbon atoms,
x is 1 to 4,
y is 1 to 7,
A is a triisocyanate radical of the following formulae

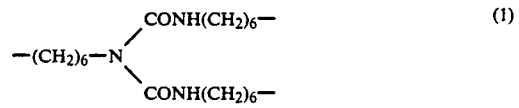

(1)

M is a member selected from the group consisting of H, alkali metal ions, ammonium ion, and organoammonium ions.

* * * * *